(12) United States Patent
Kerrigan et al.

(10) Patent No.: US 8,663,969 B2
(45) Date of Patent: Mar. 4, 2014

(54) HYBRID MUSHROOM STRAIN J9277, ITS DESCENDANTS, AND RELATED METHODS

(75) Inventors: Richard W. Kerrigan, Kittanning, PA (US); Mark P. Wach, Allison Park, PA (US)

(73) Assignee: Sylvan America, Inc., Kittanning, PA (US)

( * ) Notice: Subject to any disclaimer, the term of this patent is extended or adjusted under 35 U.S.C. 154(b) by 45 days.

(21) Appl. No.: 12/712,287

(22) Filed: Feb. 25, 2010

(65) Prior Publication Data

US 2010/0154079 A1    Jun. 17, 2010

Related U.S. Application Data

(63) Continuation-in-part of application No. 12/380,199, filed on Feb. 25, 2009, now abandoned, and a continuation-in-part of application No. 11/433,178, filed on May 12, 2006, now Pat. No. 8,084,244.

(60) Provisional application No. 60/680,774, filed on May 13, 2005, provisional application No. 60/682,189, filed on May 17, 2005.

(51) Int. Cl.
*A01G 1/04*  (2006.01)
*C12N 1/14*  (2006.01)
*A01H 15/00*  (2006.01)

(52) U.S. Cl.
USPC ............................ 435/254.1; 47/1.1; 800/297

(58) Field of Classification Search
USPC .......................... 800/297; 435/254.1; 47/1.1
See application file for complete search history.

(56) References Cited

U.S. PATENT DOCUMENTS

| 4,996,390 | A  | * | 2/1991 | Dahlberg ...................... 800/297 |
| 6,343,435 | B1 | * | 2/2002 | Moquet et al. ................... 47/1.1 |

OTHER PUBLICATIONS

Kerrigan et al. The indigenous coastal Californian population of the mushroom *Agaricus bisporus*, a cultivated species, may be at risk of extinction. Molecular Ecology (1998) 7, 35-45.*

* cited by examiner

*Primary Examiner* — June Hwu
(74) *Attorney, Agent, or Firm* — REnner Kenner Greive Bobak Taylor Weber

(57) ABSTRACT

A mushroom culture of *Agaricus bisporus* produced by hybridization of a first strain and a second strain of *Agaricus bisporus*, wherein at least one of said first and second strains of *Agaricus* is a hybrid mushroom culture of *Agaricus bisporus* designated strain J9277. Diverse additional strains can be developed from J9277 by various means including somatic and tissue culture selection, basidiospore selection, and hybridization to other strains of *Agaricus bisporus*, and the resulting derivative strains can be screened for desirable commercial characteristics. One resultant class of the mushroom *Agaricus bisporus* (J. Lange) Imbach is the hybrid strain J10165. It exhibits an attractive appearance that includes a smooth, bright white cap, and is biologically incompatible with strains of the 'U1' lineage group. A method for improving facility hygiene and reducing disease incidence at any commercial *Agaricus bisporus* mushroom production facility is also provided.

7 Claims, No Drawings

HYBRID MUSHROOM STRAIN J9277, ITS DESCENDANTS, AND RELATED METHODS

RELATED APPLICATIONS

This application is a continuation-in-part application of U.S. patent application Ser. No. 12/380,199, filed Feb. 25, 2009, now abandoned, the disclosure of which is incorporated by reference, and is a continuation-in-part application of pending U.S. patent application Ser. No. 11/433,178, filed May 12, 2006, the disclosure of which is incorporated by reference and which claims the benefit of U.S. Provisional Patent Application No. 60/680,774 filed May 13, 2005, now abandoned, and U.S. Provisional Patent Application No. 60/682,189 filed May 17, 2005, now abandoned.

TECHNICAL FIELD

This invention relates to a novel class of hybrid cultures of the edible, cultivated mushroom fungus *Agaricus bisporus* (Lange) Imbach. More particularly, this invention relates to a newly developed hybrid strain designated J9277 and to cultures that are descended or developed, either in entirety or jointly as hybrids with various strains of *Agaricus bisporus*, from J9277.

BACKGROUND OF THE INVENTION

The edible mushroom *Agaricus bisporus* (Lange) Imbach var. *bisporus*, a basidiomycete fungus, is widely cultivated around the world. In Europe and North America, it is the most widely cultivated mushroom species. The value of the annual *Agaricus bisporus* mushroom crop in the United States was about $920,000,000 in 2003-2004, according to the National Agricultural Statistics Service, Agricultural Statistics Board, U.S. Department of Agriculture (Aug. 16, 2004). More than 90 percent of the *Agaricus* mushrooms cultivated in the United States, Europe, and elsewhere have a white pileus color, in accordance with consumer preferences.

Approximately 25 years ago, the first two white hybrid strains of *A. bisporus*, developed by a laboratory at Horst, the Netherlands, were introduced into commercial cultivation. These two "Horst" strains, called U1 and U3, are closely related crosses between two pre-existing white cultivated strains, as per M. Imbernon et al., *Mycologia*, 88(5), 749-761 (1996), herein incorporated by reference. The U1 and U3 strains, while still cultivated at present, are additionally thought to be the direct progenitors of all other white *A. bisporus* mushrooms currently cultivated in most regions of the world. Commercial mushroom strains developed from U1 and U3, such as A15 and S130, are all either clones or quasi-clones of U1 or U3, being developed either by clonal vegetative propagation or from spores which retain the great majority of the parental genotype, as shown by R. W. Kerrigan et al. in *Genetics*, 133, 225-236 (1993), herein incorporated by reference. A group of strains developed either by cloning or by spore propagation, or both, from a single progenitor (as opposed to outcrossing between two different progenitors) is called a lineage group. Except for minor acquired genetic differences all white strains developed within the Horst U1 lineage group and Horst U3 lineage group share a single basic genotype with the original U1 or U3 strains, respectively (which are themselves very similar, due to their close relationship). For these reasons, and the fact that the Horst U3 lineage group is presently cultivated to a much smaller extent than the Horst U1 lineage group, modern white *Agaricus* mushroom cultivation is effectively a monoculture. Hence, for purposes of this disclosure, all of these cultivar strains will be described hereinafter as the "Horst U1/U3 lineage group" where both the Horst U1 lineage group and Horst U3 lineage group are implied.

Currently, one of the most commercially successful representatives of the Horst U1/U3 lineage group is a strain designated A15 by the assignee of record. That strain, specifically, is from the Horst U1 lineage group.

The introduction of new varieties of white *Agaricus bisporus* mushrooms into commercial culture has been impeded by three difficulties. First, cross-breeding strains of *Agaricus bisporus* var. *bisporus* can be difficult and cumbersome. U.S. Pat. No. 5,304,721 sets forth many of the problems associated with cross-breeding. Second, experience indicates that most wild germ plasm resources for this species exhibit various traits that would be unacceptable in the marketplace. Third, most of these germ plasm resources incorporate alleles that give rise to brown mushrooms, which are in less demand by consumers than are white mushrooms. Color is predominately determined by alleles at the Ppc-1 locus; see P. Callac et al., *Fungal Genetics and Biology*, 23(2): 181-188 (1996), herein incorporated by reference. Alleles providing the white color trait are rare to relatively uncommon in most wild populations of *A. bisporus*. Of approximately 150 wild *Agaricus bisporus* mushroom strains collected in coastal California, only 2 were white, while the rest were brown, as seen in, inter alia, R. W. Kerrigan and I. K. Ross, *Mycologia*, 81(3):433-443 (1989), R. W. Kerrigan et al., *Molecular Ecology*, 7:35-45 (1999), herein incorporated by reference.

The difficult nature of breeding a commercially successful hybrid variety of *A. bisporus* is illustrated by the fact that very few patent applications for novel hybrid *Agaricus bisporus* strains have been filed in the United States; of these, only one (i.e., assignee of record's brown hybrid strain X618, marketed as S600) enjoyed even moderate commercial success. It is believed that no novel hybrid white mushrooms other than U1 and U3 have heretofore ever been successfully introduced into commerce in the United States.

There is a wide range of potential benefits to introducing greater diversity of strains into commercial cultivation. Novel strains may exhibit novel patterns of nutritional resource utilization, different responses to environmental manipulation, precocity or different developmental schedules, and novel aesthetic and culinary properties for the consumer. Examples of traits favored by the consumer could include a smooth, bright white cap surface, a more attractive shape (i.e., more round) or a greater development of pileus tissue (i.e., greater "meatiness" or thickness). Some of these benefits may become apparent only after years of cultivation and marketing experience, for example, if a novel crop pathogen emerges.

New strains may offer improved resistance to known and emerging diseases of the crop. In particular, they are potentially more resistant to infection by established viral diseases that are transmitted by anastomosis (i.e., the fusion of fungal cells, called hyphae). Empirically, it is known that, for two individual heterokaryotic strains of basidiomycete fungi, anastomosis is often difficult and perhaps even impossible, and generally unsuccessful. This condition is called "vegetative incompatibility." A more detailed description of anastomosis and of some viral diseases to which basidiomycete fungi are susceptible can be found in A. S. M. Sonnenberg et al., *Mushroom Science* 14, 587-594 (1995), incorporated herein by reference.

Instances of incompatibility between strains of the mushroom *Agaricus bisporus*, and in other species of basidiomycete fungi, have been noted for many years. However, there is no real understanding of how this self/non-self recognition system works. It is not known for *Agaricus bisporus* how many genetic loci are involved, where they occur on the chromosomes, how many alleles are present at any locus, or what the specific effects of any allele or locus might be. Consequently it is not possible to predict what the compatibility phenotype of any new hybrid might be.

As noted above and since the 1980s, the only strains of white *Agaricus bisporus* mushrooms now grown commercially in North America and Europe, and in most other parts of the world, are strains derived from the Horst U1/U3 lineage group, and most particularly, the 'Horst U1' group. All share very similar genetic identities and all are compatible within and among the group, a situation known to agronomists as a 'monoculture'. The industry has essentially standardized on this inter-compatible group of strains, and no widely-accepted alternative white strains have been introduced since 1980.

Prior to the 1980s, when a more diverse set of commercial strains was in use, crop rotation was sometimes adopted in response to the establishment of virus disease at commercial facilities. However the current situation of monoculture has, in recent decades, made it impossible to implement a scheme of crop rotation to allow for an interruption of strain identity and compatibility at production facilities. This situation of monoculture allows pathogens to become more perfectly adapted to the host strain, and to establish reservoirs of pre-adapted infectious material, in production facilities, and, in the case of obligate intracellular pathogens including the dsRNA viruses of *Agaricus*, also allows them to pass freely from established infection reservoirs into new strain-compatible crops.

In modern mushroom production facilities, a crop of mushrooms may typically occupy production space for 46-57 days, between the planting of spawn in the compost and the emptying and cleaning of the facility to prepare for the initiation of the next crop. During that crop cycle, three 'flushes' of mushrooms are normally harvested at about weekly intervals. In some cases, the scheduling of new crop production cycles may lead to the disposal of the prior crop before three full flushes of mushrooms can be obtained. There are three potential opportunities for accelerating this crop cycle: (1) during the spawn run interval, typically of 13-16 days duration, (2) during the case run interval, typically of 15-19 days duration, and (3) during the flushing/harvest periods, typically of 18-22 days duration. There are several economic benefits that derive from a shorter crop cycle: (a) higher utilization of physical plant, and distribution of overhead costs over more crops, (b) ability to routinely complete harvest of the third flush, increasing productivity, (c) opportunity to harvest more of the crop earlier with respect to disease pressure, which impacts crop quality and value, and (d) additional scheduling flexibility represented by multiple strain-schedule options.

In some markets, mechanical harvesting is preferred due to the higher cost of human labor. In order for a mushroom crop to be suitable for mechanical harvesting, uniform development and a sufficiently long stem are necessary and desirable.

SUMMARY OF THE INVENTION

The advantages of the present invention over existing prior art relating to *Agaricus bisporus* mushrooms and cultures, which shall become apparent from the description which follows, are accomplished by the invention as hereinafter described and claimed.

Broadly, one or more aspects of the present invention may be directed to a newly developed class of *Agaricus bisporus* mushroom cultures comprising various newly developed hybrid strains descended or developed from the hybrid strain J9277. Thus, the present invention encompasses substantially all strains developed from J9277 by any means, including but not limited to single-spore cultures, multi-spore cultures, and somatic selections, and also all hybrid cultures descended from J9277, including first generation hybrid cultures and any further hybrid cultures produced from any descendents of J9277, including their descendents. In at least one embodiment of the invention, the J9277 strain, or strains descended or developed from J9277, may be crossed with a strain of, or a strain descended from, the Horst U1/U3 lineage group to form additional distinct novel hybrid cultures. Similarly, one or more other aspects of the present invention may be accomplished by a hybrid fungus culture of *Agaricus bisporus* produced by crossing a first culture of *Agaricus bisporus* with a second culture of *Agaricus bisporus*, wherein at least one of said first and said second cultures of *Agaricus bisporus* is a fungus strain designated J9277, a representative culture of said fungus strain having been deposited under ATCC Accession No. PTA-6692, or a fungus strain descended or developed from said strain J9277.

In another embodiment, the J9277 strain, or strains descended or developed from J9277, may be crossed with the B7023 strain of *Agaricus bisporus* to form a distinct novel class of hybrid cultures. In one embodiment, such a new and distinct variety of *Agaricus bisporus* mushroom is characterized by abundant production of mushrooms having smooth, white caps. The new mushroom also has a genotype that combines markers from each of its progenitors, forming a unique genotype with respect to other known white hybrid mushrooms. This novel and distinct variety of mushroom is identified as *A. bisporus* hybrid 'J10165'.

The present invention is further directed to a method for improving facility hygiene and reducing disease incidence at any commercial *Agaricus bisporus* mushroom production facility. The method comprises the steps of (1) substituting mushroom spawn incorporating a commercially acceptable first hybrid strain of *Agaricus bisporus* selected from the group consisting of hybrid strains of J9277, hybrid strains of J10165, and hybrid strains of descendents of J9277 or J10165, in place of mushroom spawn incorporating a different second strain that is then being grown at that facility, the first strain being culturally incompatible with said second strain; (2) allowing the substituted first strain of step (1) to colonize the standard compost substrate of the facility; (3) if a casing inoculant material such as "CAC" or "CI" is incorporated into the "casing soil," then substituting the same first strain in the casing inoculant as the strain that was substituted in the spawn at step (1); (4) producing a normal crop of mushrooms using cultural techniques suitable for the substituted first strain of steps (1) and (3); (5) carrying out steps (1) through (4) for every crop in every room or area of the facility for at least a sufficient number of repetitions until achieving the condition wherein the only strain present in any form at the facility is the substituted first strain.

Advantageously, it has been found that the hybrid culture J9277 produces mushrooms that exhibit commercially acceptable physical and performance characteristics. For example, J9277 has a white cap. J9277 can produce a crop of mushrooms several days earlier than existing commercial strains such as A15. J9277 can produce a longer-stemmed mushroom, relative to commercial strains like A15, which is preferred for mechanical harvesting systems. J9277 has thicker cap flesh, relative to the width of the cap, and therefore a meatier aspect, than the commercial strain A15. J9277 also has a rounder cap shape than A15.

It has also been found that J9277 can produce hybrid descendents by making crosses between J9277 and other strains of *Agaricus bisporus*. Brown hybrid descendents of J9277 can be produced by making crosses to other strains carrying an allele for the brown color at the Ppc-1 locus. Still other embodiments include a new and distinct variety of *Agaricus bisporus* mushroom characterized by abundant production of mushrooms having smooth, white caps. The new mushroom also has a genotype that combines markers from each of its progenitors, forming a unique genotype with respect to other known white hybrid mushrooms. This novel and distinct variety of mushroom is identified as *A. bisporus* (J. Lange) Imbach, and is named 'J10165'. This new hybrid mushroom variety has been asexually reproduced by vegetative mycelial propagation in Kittanning, Pa., in the breeding program of Sylvan Research, 198 Nolte Dr., Kittanning, Pa. 16201.

To vegetatively propagate the mushroom culture aseptically, under laboratory conditions, a small portion of a pure (=axenic) mycelial culture on a suitable medium, such as potato dextrose agar (PDA), is transferred to a fresh plate or tube of newly prepared, sterilized medium (for example PDA) using a sterilized instrument such as a scalpel. Any aseptic transfer of an axenic culture to fresh culture medium achieves the objective of vegetative propagation. These techniques are standard and absolutely routine in the mushroom cultivation industry.

PREFERRED EMBODIMENT FOR CARRYING OUT THE INVENTION

As noted hereinabove, the present invention relates to cultures related to the hybrid *Agaricus bisporus* strain J9277, i.e., to cultures developed from J9277 directly, and to cultures that are descendents of J9277 produced via hybridization of either the J9277 strain itself, or strains developed from the J9277 strain, to a second strain of the species. It will be understood that the term "descended" is specifically intended to mean genealogically descended from the strain rather than evolutionary descent, the latter being a naturally occurring process of genetic divergence typically involving at least hundreds of generations and thousands of years. It will be further understood that the term "developed from" is meant to include derivation by any means of selection or manipulation of any element of the starting material, in this case a mushroom culture of *Agaricus bisporus*. Also, it will be understood that the terms "strain," "culture," and "variety" can be used essentially interchangeably for this invention, but attempts have been made to maintain a distinction between the terms based on context. For purposes of this invention, "strain" has been generally used when discussing the more abstract, genealogical composition of matter; "culture" has been generally used when discussing the actual physical embodiment of the composition of matter to be grown typically on a sterile medium; and "var." (i.e. "variety") has been generally used when discussing the particular taxonomic variety of *Agaricus bisporus*. The term "variety," as used in many U.S. plant patents, is essentially equivalent to "strain."

Hybridization of *Agaricus bisporus* cultures of the invention may be accomplished by allowing two different cultures, one of which is strain J9277 or a strain descended from the strain J9277, to grow together in close proximity, preferably on sterile media, until anastomosis (i.e., hyphal or cell fusion) occurs. In one embodiment, both cultures brought together for crossing purposes will be haploid homokaryons. Where two compatible nuclei (i.e., two nuclei carrying different alleles at the Mat locus, which determines mating type) are present in a fusion cell, they jointly proliferate and establish a growing heterokaryotic culture. This process is commonly known as crossing. Where each of the two nuclei in the resulting heterokaryotic culture was contributed by a different parental strain participating in the fusion process, then the new heterokaryon is a first-generation outcrossed hybrid offspring of the two parents. That is, where the J9277 strain is one of the parental strains and is crossed with another parental strain of *Agaricus bisporus*, the resultant hybrid is a first-generation outcrossed hybrid culture defined as one embodiment of the present invention.

Due to the vegetative incompatibility that often exists between pairs of heterokaryons (i.e. strains each incorporating two compatible nuclei), the preferred method of hybridization uses two haploid strains (i.e., homokaryons), one being obtained from each non-haploid (i.e., heterokaryotic) parental strain. Haploid strains, which incorporate only a single type of nucleus, hybridize with a higher frequency of success, and produce offspring with only a single, predictable, nuclear genotype, in contrast to fusions involving heterokaryons. Homokaryons may be developed from parental strains via several methods including generation of protoplasts, isolation of hyphal tips, or from germinated spores. The latter method provides homokaryons with diverse genotypes, as a result of meiotic recombination during sporogenesis. All of the foregoing methods can also be employed to develop cultures of heterokaryon selections of J9277 that can produce crops of mushrooms and accomplish various aspects of the invention.

Unlike homokaryons, heterokaryon cultures are capable of producing mushrooms and are routinely incorporated into commercial products such as mushroom spawn and casing inoculant as described below. They can also serve as the progenitors of future generations of inbred and outcrossed descendants. Thus, the present invention provides for the crossing of strains descended from the J9277 strain as well. 'Inbred' is used broadly here to include self-fertilized heterokaryon progeny from spores of a single parent as well as offspring between a hybrid and itself or one of its own progenitors. An uncommon class of aneuploid offspring with a fractional chromosomal complement between 1n and 2n, therefore not clearly homokaryons or heterokaryons, has also been documented in *Agaricus bisporus* by Kerrigan et al. (Mycologia 84(4):575-579, 1992, herein incorporated by reference).

J9277 is a fourth-generation hybrid descended from the tetrasporic brown wild parent strain JB137, which belongs to the taxonomic variety *Agaricus bisporus* var. *burnettii*, and the commercial white parent strain U1, which belongs to *Agaricus bisporus* var. *bisporus*. The first generation crosses between JB137 and U1 produced a series of brown hybrid strains; after screening these, hybrid strain J1229 was selected for further development.

In the second hybrid generation, crosses between J1229 and U1 produced a series of hybrids that were either brown or white, depending on their inherited genotype. After screening these hybrids, the second generation hybrid strain J5466 was selected for further development.

Contemporaneously, another first generation hybrid was produced from crosses between wild bisporic parent strain RWK 1634 and the white commercial parent strain known as White Queen 101. Several hybrid offspring of these crosses were screened, and hybrid strain B5069 was selected for further development.

In the third hybrid generation, parent strain J5466, which carries two white alleles, was crossed with parent strain B5069, which also carries two white alleles. A series of white hybrid strains was produced, and after screening, hybrid strain J6211 was selected for further development.

To create the fourth generation hybrid strain J9277, the homokaryon J6211-s4, obtained from hybrid parent strain J6211, was mated with homokaryon S130-d, from the Sylvan white commercial parent strain S130. The product of the successful cross was designated J9277. Crops of J9277 were produced, and the culture of J9277 was re-established from tissue explants from mushrooms obtained from these crops, demonstrating the equivalent cultural potential of mushrooms and mycelium.

A deposit of a culture of hybrid strain J9277, as disclosed herein, has been made with the American Type Culture Collection (ATCC), 10801 University Boulevard, Manassas, Va. 20110. The date of deposit was May 3, 2005. The culture deposited was taken from the same culture maintained by Sylvan, Inc., Kittanning, Pa., the assignee of record, since prior to the filing date of this application. All restrictions upon the deposit have been removed, and the deposit is intended to meet all deposit requirements of the U.S. Patent and Trademark Office, including 37 C.F.R. Sec. 1.801-1.809, and all deposit requirements under the Budapest Treaty. The ATCC Accession No. is PTA-6692. The deposit will be maintained in the depository for a period of 30 years, or 5 years after the last request, or for the effective life of the patent, whichever is longer, and will be replaced as necessary during that period. The strain will be irrevocably and without restriction or condition released to the public upon the issuance of a patent on this strain.

It will be understood that a culture of *Agaricus bisporus* will produce mushrooms (=basidiomata) only under the appropriate conditions. Those conditions necessary to produce mushrooms from such a culture are well known to those having ordinary skill in the art, and can be determined without undue experimentation. *Agaricus bisporus* mushrooms are customarily produced according to the following process, although any method known in the art for fruiting the cultures can be employed. A pure culture incorporating a single mushroom strain is clonally propagated on a sterile medium. This culture is a mycelium comprising many microscopic, threadlike elements called hyphae, which are themselves composed of cellular compartments. For commercial purposes, some of the pure culture is transferred to a larger volume of an appropriate medium which, when fully grown, can be used as inoculum to produce commercial products such as spawn and casing inoculant (technically all forms of the pure culture are inoculum in a broad sense). Mushroom spawn is usually prepared from a sterilized cooked grain such as rye, wheat, or millet, which may be amended with other materials such as chalk. Casing inoculant is typically composed of particulate matter such as peat moss, vermiculite, and/or compost, blended with some nutrients and moistened with water. A small volume of inoculum is mixed with a larger volume of sterilized grain (for spawn) or other substrate (for casing inoculant). When the pure culture mycelium has grown throughout and fully colonized the larger volume of sterilized substrate, the resulting mass of substrate plus mycelium is now a conventional commercial product, either spawn or casing inoculant. It will be understood that these mushroom producing products can be produced from strains descended from J9277 as well. For example, many of these products can be produced from the hybrid strain J10165 as described below.

To produce a crop of mushrooms, the mushroom farmer combines a small volume of mushroom spawn with a larger volume of pasteurized compost in a purpose built structure. Conventional compost is prepared from straw plus water, one or more nitrogen sources, and inorganic calcium sources. Preparation of compost typically takes two to three weeks, culminating in a period at elevated temperatures sufficient to kill invertebrates and many undesirable fungi and bacteria. Once spawned, about 13 to 16 days are required for the compost to become fully colonized by the mycelium. At this stage, a layer of porous, absorbent, low-nutrient material such as soil or peat moss is placed over the compost to a depth of about 2 inches. This layer, called the "casing," may preferentially incorporate casing inoculant or another source of mushroom mycelium such as colonized compost, to speed and enhance the crop. It is important to use the same strain in the spawn/compost and the casing inoculant. Development of the mushroom mycelium in the casing, and formation of mycelial strands and mushroom primordia, takes approximately 7-10 days. Subsequently the mushrooms will enlarge during the fruiting process, which requires about 7-10 days more to produce mushrooms mature enough for harvest and sale. Additional crops, called flushes or breaks, will be produced at approximately weekly intervals. Modern farmers find that taking three flushes is most profitable.

To create hybrid descendents of J9277, homokaryons obtained from J9277 were crossed with homokaryons from a second parent strain of *Agaricus bisporus*. If not already explicit, it will further be appreciated that hydridization can further occur between two different *Agaricus bisporus* cultures wherein one of the cultures is the J9277 strain or is descended or developed from the J9277 strain. Thus, all progeny, descendents, and selections of the J9277 strain may be used in further crosses. In mushroom breeding, mycelial (=vegetative) cultures of two compatible progenitors (typically these are haploid homokaryotic strains called homokaryons) must come into physical contact so that one or more fusion zones can occur between the progenitors. Within those fusion zones nuclei and organelles from the two progenitors become associated. In *Agaricus bisporus*, a novel, hybrid mycelium ultimately containing two compatible haploid nuclear types (one from each of the two progenitors) plus one mitochondrial type (from either one of the progenitors) emerges. This novel hybrid mycelium can be isolated and propagated to provide the new hybrid culture, which can be further subdivided and propagated for commercial or other purposes.

In order to demonstrate practice of the invention, a hybrid strain of J9277 was crossed with a second strain of a different *Agaricus bisporus* culture, namely, B7023. The resultant hybrid is a hybrid of the present invention, named J10165. Again, this cross is between homokaryons obtained from two parental heterokaryotic strains, J9277 and B7023. As noted above, J9277 is the product of several generations of hybridization among diverse strains, including one tetrasporic wild progenitor as described in U.S. Pat. No. 5,304,721. A series of single-spore homokaryons (haploid offspring) was prepared from a spore print from J9277, and one of these, called the J9277-s45b homokaryon, was used in the J10165 cross.

The second homokaryon in the cross that produced J10165 is 'B7023-s7'. B7023 is itself a hybrid strain owned by the Assignee of record, produced by the cross of wild homokaryon 'I3-s13,' isolated from a collection ('I3') from Israel, and homokaryon 'S130-b,' isolated from Sylvan's commercial hybrid strain S-130 in the U1 lineage group.

The cross was made by placing the homokaryons 'J9277-s45b' and 'B7023-s7' in close proximity on a sterile culture medium, allowing the two cultures to grow and contact each other, anastomose, and establish the hybrid heterokaryotic strain J10165, which was then clonally propagated.

The pedigree of J10165 was confirmed by the ITS1+2 DNA sequence fingerprint. The positional notation for the *Agaricus bisporus* ITS1+2 DNA segment is taken from M. Challen et al., 95(1): 61-73 (2003), incorporated herein by reference. The presence of both C and T bases at 5 positions (52, 150, 153, 522, 563) in the ITS1+2 segment of J10165 demonstrates the presence of two homologous chromosomes, one contributed by 'J9277-s45b' and the other by 'B7023-s7,' each one of which carries either a C (only) or a T (only) at each specified position.

The performance characteristics and appearance of mushrooms produced in commercial cultivation will vary, depending on the properties of cultivation materials (compost, e.g.) used, crop management techniques employed, and environmental conditions such as air velocity, humidity, and $CO_2$ level. Some general characteristics of J10165 are similar to those of other commercially successful white hybrid mushroom strains, for which the A-15 hybrid strain may serve as an example. The timing of harvest of J10165 is within 36 hours of that of A-15, either faster or slower depending on growing conditions, and the yield is also comparable within a narrow range that is affected by specific conditions. The size and the proportions of the mushrooms may or may not be statistically different between the two strains, depending upon culture conditions; both produce many medium to large mushrooms by commercial grading standards, with broadly rounded caps. All of these traits are demanded by a large segment of the commercial market for mushrooms, and these similarities between J10165 and other commercial strains are a deliberate result of a particular selection and breeding strategy.

J10165 can be distinguished from existing commercial hybrid white mushroom strains by at least three characteristics. First, it has a smoother cap than A-15. The cap of J10165 will remain smooth and even exhibit a reflective luster where its cap curvature is greatest, under conditions in which A-15 will develop a rough, scaly, non-lustrous cap surface. These traits can be observed in the drawing.

Second, J10165 exhibits vegetative incompatibility toward A-15, eliminating or greatly reducing the possibility of anastomosis between J10165 and current commercially grown strains. Consequently, it is expected that this will also prevent or greatly reduce the transmission or exchange of cytoplasmic elements including pathogenic viruses. This incompatibility can be demonstrated by confronting the two strains in cultivation. In commercial cultivation, an inoculum of the desired strain (spawn) is introduced into a prepared compost substrate and colonization proceeds for about two weeks. At that time, a layer of casing mix or 'soil' is applied to the upper surface of the compost to stimulate and support the production of a mushroom crop. Normally, a second inoculum ("CI" or "CAC") of the same strain is introduced into the casing mix in order to speed and regularize the development of the mushroom crop. If two inocula constituting an incompatible combination are successively introduced, one into compost and the other into casing, the resulting antagonistic response reduces the production of mushrooms and/or delays their appearance, particularly away from the edges of the growing trays. This incompatibility response is the norm when two non-identical strains are used in this way.

The following Table I presents the results of Experiment 08-595, in which J10165 and A-15 were cultivated using compatible and incompatible combinations of inocula. All of the typical incompatibility responses were observed.

TABLE I

Effects of combining inocula of 'J10165' and 'A-15' in compatible (self + self) and incompatible (self + non-self) combinations.

| | Compost inoculum | | | |
|---|---|---|---|---|
| | J10165 | J10165 | A-15 | A-15 |
| | | Casing inoculum | | |
| | J10165 | A-15 | J10165 | A-15 |
| Total yield (% average, in g) | 119% | 107% | 75% | 114% |
| Days until first harvest | 16-17 | 16-17 | 18 | 17 |
| First mushrooms only at edges of trays? | no | yes | yes | no |

The observed incompatibility indicates that J10165 will be less susceptible to infection by any "intergroup" contact with spores or mycelium of strains in the U1 lineage group, relative to the susceptibility of current commercial white hybrids strains in "intragroup" contacts with the same or other strains that are members of the commercially predominant U1 lineage group.

Third, J10165 incorporates a unique ITS DNA sequence fingerprint that distinguishes it from other known white hybrid mushrooms, namely, the presence of both C and T bases at positions 52, 150, 153, 522, and 563, both A and G bases at position 32, and a T base at position 461 in the ITS1+2 DNA segment of J10165. This fingerprint is unique with respect to those of the U1/U3 lineage groups and also to those of hybrid strains B7970 and J9277 noted above. This fingerprint permits the identification of J10165 in both vegetative culture (e.g. inoculum, spawn, CI and CAC) and also in the mushroom stage as well. The uniqueness of this DNA segment is also indicative of the genetic novelty expected to characterize the entire genome. This supports the belief that other valuable novel characters may become evident as more experience is gained.

The J10165 strain provides for the abundant production of mushrooms having smooth, white caps. As the Royal Horticultural Society (RHS) color charts do not provide a reference standard for the color "white", direct measurements of color of the J10165 mushroom cap have been made using a Minolta Chromometer and the L-a-b color space system. Four measurements were made on the caps of each of seven mushrooms grown in a testing facility. The mean values, plus or minus the standard error, for the measured L, a, and b color components were as follows: L=91.7±0.19; a=−0.44±0.07; b=10.8±0.21. Colors within or substantially coinciding with the color space described by these three parameter distributions are called "white" according to standard and accepted practices of the commercial mushroom industry.

A formal description of the mushrooms produced by strain J10165 follows: Basidiomata agaricoid. Pileus at harvest stage broadly convex, 30-75 mm broad, surface white, glabrous and often lustrous. Flesh firm, white, typically 12-16 mm thick. Lamellae free, close, initially pallid, becoming dark chocolate brown, about RHS 187A-RHS 200A, as maturation progresses. Veil forming a thick, relatively inelastic, intermediate (semi-band-like with a wedge-shaped cross section) white annulus, smooth or obscurely striate above, smooth or floccose below. Stipe white, smooth, equal or slightly enlarged at base, 16-21 mm broad, length variable in response to cultural influences but often ca. 2.5 times the stipe thickness, interior stuffed-hollow. All parts generally do not develop pronounced non-white colors when rubbed, crushed or cut. Chemical reactions: KOH negative (not yellowing), Schaffer's Reaction (aniline×HNO$_3$) negative (neither yellow, red nor orange). Microscopic features are as previously described for the species in Kerrigan, R. W., *The Agaricales of California*. Vol. 6. Agaricaceae, Mad River Press, Arcata, Calif., 1986, the disclosure of which is incorporated herein by reference and as understood by those having ordinary skill in the art for the species *Agaricus bisporus*.

In order to demonstrate practice of the invention as it relates to J9277, a subculture of strain J9277 was propagated as described above to produce spawn and casing inoculant. This was used in a series of tests in Sylvan facilities that produced data on the desirable commercial properties of strain J9277.

It was observed regularly that crops of J9277 were ready to harvest 1 to 2.5 days earlier than commercial control strain A15. For example, in one test, in a facility that employs a relatively accelerated cropping schedule, J9277 produced a heavy crop 13 days after casing, while A15 produced a light harvest on day 14 and a moderately heavy crop on day 15. This pattern was also observed in trials at independent test sites, where a two day speed advantage for J9277 over A15 was typical.

Also observed in trials at independent test sites was the earlier readiness of J9277, relative to A15, for the application of casing material. For example, at one test site, where commercial operations use a 16-day spawn run period prior to casing for the A15 strain, best results have been obtained using a 12-day spawn run for J9277.

An additional regular observation from trials of J9277 is that the harvest of each of three flushes of mushrooms obtained from a single spawning of compost can be concluded promptly, at regular intervals. This means that the entire third flush can be reliably harvested prior to the scheduled termination of the crop, allowing maximum product harvest while maintaining the facility schedule. This is sometimes a problem with other commercial strains. The entire third flush of mushrooms produced by J9277 has typically been harvested on day (17-)18 of the harvest period.

In aggregate, J9277 can save 2-4 days in spawn run, 1-2 days from case to crop, and 0-4 days during the cropping period. A realistic net observed gain of about 7 days represents about 12-15% of the total crop turnaround time required by conventional strains, allowing a corresponding improvement in the efficiency of facility utilization. Facility scheduling can be more flexible, and a full third flush can be harvested even on a tight schedule. Accelerated cropping also allows more of the crop to be obtained under conditions of relatively lower disease pressure.

Measurements of physical dimensions of mushrooms produced by J9277 show differences from mushrooms produced by A15. Equal numbers of mushrooms of both strains, grown at the same time in the same environment and conditions, were measured. Proportional measures (ratios of two direct measurements) were calculated because absolute dimensions vary widely among mushrooms of any strain, and are influenced by cultural factors. (1) 'Cap Width' (CW) is defined here as the greatest horizontal distance between two vertical lines tangential to either side of the cap. (2) 'Cap Flesh Thickness' (CFT) is the vertical distance from the top of the lamellae (i.e., gills) adjacent to the stipe, to the surface of the pileus directly above. (3) 'Cap Fleshiness' (CF) is calculated here as CFT/CW. (4) 'Cap Height' (CH) is the vertical distance between two lines that are horizontal and tangential to the lowest and highest portions of the cap, respectively. (5) 'Cap Roundness' (CR) is calculated here as CH/CW. (6) 'Stem Length' (SL) is the distance from the bottom of the stem to the boundary between the stem and cap structures. (7) 'Proportional Stem Length' (PSL) is calculated here as SL/CW.

A t-test was used to assess the statistical significance of the observed differences. These data are summarized in TABLE II set forth hereinbelow.

TABLE II

Measurements of Mushroom Size and Shape

| Measure | Mean, J9277 | Mean, A15 | p value: J9277 t-test | vs A15 |
|---|---|---|---|---|
| Cap Width (CW) | 41.2 mm | 47.6 mm | NA | NA |
| Cap Flesh Thickness (CFT) | 12.95 mm | 13.35 mm | NA | NA |
| Cap Fleshiness (CF = CT/CW) | 0.317 | 0.283 | 0.0051 | +12.0% |
| Cap Height (CH) | 24.4 mm | 25.5 mm | NA | NA |
| Cap Roundness (CR = CH/CW) | 0.59 | 0.54 | 0.0001 | +11.0% |
| Stem Length (SL) | 39.5 mm | 41.6 mm | NA | NA |
| Pr. Stem Length (PSL = SL/CW) | 0.96 | 0.88 | (0.056) | +9.7% |

Cap Fleshiness in J9277 was about 12% greater than in A15 (p=0.0051). Mushrooms of J9277 appear to be correspondingly more 'meaty' than those of A15. This is an appealing consumer trait. Cap roundness was about 11% greater in J9277 than in A15 (p=0.0001), and this is also likely to appeal to the consumer. These differences were highly statistically significant.

In this sample, the Proportional Stem Length, or ratio of SL/CW, was about 9% greater in J9277 than in A15. This difference approached the accepted threshold of statistical significance (p=0.056). Under other cultural conditions J9277 has been observed to produce mushrooms with a greater absolute stem length (SL) in combination with a tightly closed cap, a combination that is desirable for mechanical harvesting.

To determine whether the sample size of ten mushrooms per strain had limited the power of the t-test to demonstrate the statistical significance of any difference, two measurements were repeated on a larger sample of twenty mushrooms per strain from another test crop that included treatments of both A15 and J9277. The results are presented in Table III.

TABLE III

Measurements of Mushroom Size and Shape

| Measure | Mean, J9277 | Mean, A15 | p value: J9277 t-test | vs A15 |
|---|---|---|---|---|
| Cap Width (CW) | 39.9 mm | 45.5 mm | NA | NA |
| Stem Length (SL) | 38.1 mm | 31.9 mm | 0.0007 | +19% |
| Pr. Stem Length (PSL = SL/CW) | 0.97 | 0.72 | 0.00002 | +36% |

It is evident from the direct measurements of CW and SL that conditions for the test crop that produced the mushrooms measured for Table III favored the development of a longer stem in J9277, relative to the sample reported in Table II. For PSL, J9277 had a 36% advantage over A15, and a highly significant difference in a t-test (p=0.00002). J9277 also had a 19% (=6 mm) advantage over A15 in absolute stem length (SL; p=0.0007). Although proportional measurements (=ratios) are preferred when size of the mushroom is an irrelevant source of variability, the absolute stem length is commercially and economically important. For example, mechanical harvesting favors a longer stem. From the data presented in Table III, J9277 is shown to be better suited than A15 for mechanical harvesting.

As a consequence of having wild strains JB 137 and RWK 1634 as ancestors, J9277 and all related hybrid strains belonging to the class of the invention carry distinctive genetic markers not found in the Horst U1/U3 lineage group. For example, the new hybrid variety J9277 has a novel DNA sequence in the Internal Transcribed Spacer regions (ITS1+2) of the nuclear rRNA gene complex. There are five relevant polymorphisms in the sequences of *Agaricus bisporus*, at positions 52, 253, 461, 522, and 563 of the nominal *A. bisporus* var. *bisporus* sequence, which is numbered from the initial 5☐ 'G' (=position 1) in the sequence GGAAGGATCA near the 3☐ end of the 18S rRNA gene. TABLE IV provides the allelic states of relevant members of the J9277 pedigree, and of the S130 member of the Horst U1/U3 lineage group.

TABLE IV

ITS1 + 2 alleles of the J9277 pedigree and of S130

| Strain | Allele(s) | Sequence (positions 52, 253, 461, 522, 563) | | | | |
|---|---|---|---|---|---|---|
| JB 137 | C + D | C | A | T | C/T | C |
| RWK 1634-s3 | A | C | G | A | C | C |
| J6211-s4 | A | C | G | A | C | C |
| S130b | E | C | G | T | T | T |
| S130d | B | T | G | T | T | T |
| J9277 | A + B | C/T | G | A/T | C/T | C/T |
| S130 | B + E | C/T | G | T | T | T |

From TABLE IV it will be seen that allele A, present in ancestral homokaryon RWK 1634-s3, was inherited by J6211-s4, and subsequently by J9277. J9277 also inherited allele B from homokaryon S130d. The A+B genotype of J9277 is novel and distinct from the B+E genotype of the Horst U1/U3 lineage group, as exemplified by S130.

It would be expected, based upon averages, that about 12.5% of the nuclear genome of J9277 was inherited from the wild strain RWK 1634, and about 6.25% was inherited from the wild strain JB 137. Thus the genome of J9277 comprises a unique and novel combination of genetic material from its progenitors. The actual amounts of genetic material, in J9277, contributed by each ancestor in the first and second generations of the pedigree is difficult to determine precisely, and is expected to vary among hybrids of each subsequent generation.

From TABLE IV it is clear that J9277 can be distinguished from currently marketed white-capped strains of *Agaricus bisporus* by its genotype, in addition to the other distinctive characteristics discussed hereinabove. Data presented herein is non-limiting as these are only examples of useful markers; several others have been documented. It is important to note that all hybrids belonging to the invented class will have novel genotypes due to the presence of genetic material from JB 137 and RWK 1634; however those genotypes may differ from the example of J9277 presented above. Further, in subsequent outcrossed, backcrossed, and selfed generations the proportion of genetic material and markers from J9277 may change. In selfed progeny, a heterozygous marker may become homozygous, producing the appearance of a novel genotype, whereas in actuality a nearly complete subset of the original genotype will be present. For these reasons, although genetic markers can readily identify members of the invented class, and genotypes will normally remain stable attributes of individual strains within the class, no specific genotype is represented to be an invariable attribute of the class as a whole.

In order further to demonstrate practice of the invention, four homokaryons were obtained from single spores of hybrid strain J9277. These four homokaryons were crossed with a homokaryon obtained from another strain that is a hybrid descendent of Horst U1. The 4 resulting hybrids had brown caps, demonstrating that novel traits can be introduced into descendents of J9277 via hybridization. The resulting hybrids can be evaluated for economically valuable traits as described above.

In yet a further demonstration, cells from lamellar tissue blocks of J9277 were transformed to hygromycin resistance via an *Agrobacterium tumefaciens*-facilitated protocol using the plasmid vector pBGgHg, which contains the hpt gene under the control of an *Agaricus bisporus* gpd promotor, as described in Chen et al. (2000), the disclosure of which is incorporated herein by reference. Transformed cell lines were confirmed by virtue of their ability to grow on agar media containing hygromycin, whereas the untransformed wild-type J9277 did not grow on this medium. 35 transformed cell lines were produced. One transformed J9277 cell line was used to prepare grain spawn that was used to inoculate compost. A mushroom crop with the typical behavior and appearance of J9277 was produced from the inoculated compost. A tissue culture of one of these mushrooms was generated and it maintained the hygromycin-resistant phenotype on the selective agar medium, showing that the introduced trait was stably expressed. These results demonstrate that J9277 can be used as a system for the production of heterologous proteins via DNA-mediated transformation.

Based on the foregoing disclosure, it should now be apparent that producing novel *Agaricus bisporus* mushroom strains by enabling hybridization between hybrid strain J9277 and other strains of *Agaricus bisporus*, including those strains belonging to the Horst U1/U3 lineage group, will carry out yet other objects of the present invention.

In addition to commercially acceptable characteristics, some of these hybrid strains will have other commercially valuable characteristics, such as resistances to crop diseases and/or antagonism to heterokaryon stains of the Horst U1/U3 group or to other commercially used strains, leading to reduced susceptibility to infection with viral diseases. Such characteristics can enable a method of hygiene improvement.

It was noticed that some white hybrids of interest exhibited some degree of antagonism toward strains such as A-15 in the U1 group. However, there was and still is no way to predict which new hybrids will exhibit this trait, or to what degree. In fact, an accepted, standardized screening protocol to assess this potential trait in new hybrids has not been established, although the assignee of record is engaged in the development of such methods. Observations of this trait in what is so far a small number of new hybrids have been the result of serendipity.

In trials of the hybrid strain J10165 it was noted that the adjacent trays of the A-15 control strain were often afflicted with large bare areas where few or no mushrooms developed. After eliminating other possible explanations, it was proposed that carry-over of traces of J10165 culture from those trays to the following trays of A-15 as they moved down the processing line might be responsible. This idea was tested by placing approximately one gram of J10165 culture in compost, onto the surface of isolated trays of A-15 compost, before the casing soil was applied. This treatment produced a bare circle of up to about 20 cm to about 30 cm diameter, centered on the point where the J10165 material was placed. This unexpected outcome demonstrates a very strong antagonism between the two strains, such that hyphal fusion (anastomosis) that would permit the transmission of virus particles and the infection of the incompatible culture becomes much more unlikely. At present there is no method to quantify this effect.

However, a qualitative test has been designed to establish whether two different strains of mushrooms are compatible with each other, i.e. whether mycelia from the two different strains will anastomose resulting in the production of fruit bodies. The test has been designed so that more than two strains can be tested at any time. This method is currently in an early stage of evaluation.

In practice, a single tray with a surface area of 15.55 ft$^2$ will be filled with compost spawned with 1 mushroom strain which is referred to as the base spawn. A Perspex sheet with 25 individual rings measuring 6 inches in diameter×1½ inches deep is then placed on the compost surface, thus creating 25 individual test plots per tray. A minimum of 5 plots should be used for any one strain.

Ten rings/plots currently were then filled with a traditional black peat casing layer containing casing inoculum matching the spawn strain used as the base spawn to act as the control for the tray proving compatibility. Three different strains were then cased in groups of five plots in order to complete the tray test. The test can be replicated using a variety of base spawns in additional trays. Casing inoculum is mixed in to the casing at the current rate of about 375 grams of compost per square meter. It is vital during the casing process that every precaution is taken to ensure no cross contamination takes place. No casing material or inoculum designed for a set of plots can come in contact with casing material, inoculum or rings of another set of plots. All test plots were watered on the day of application then grown using parameters used in commercial mushroom production.

Visual observations were made daily, including strength of mycelium growth, pin production and timing of any crop. Photographic evidence was also gathered. In the example test, the base spawn within the trays was J10102 and the three strains selected to test for compatibility in the 3 remaining 5 plot tests were commercial A15, J1901 and J10165. Further tests will be conducted in the future for example W10432, J1901 and J10165, all used as the base spawn in separate trays.

If, as a result of these tests, it is visually evident that no fructification occurs on any given plot, the combination of the strain in the base spawn and the strain in the casing layer will be deemed to be incompatible.

Consequently, it is believed that if such strains comprising the invention, for example J10165, combining commercially acceptable traits with the additionally useful trait of resistance to infection or to the effects of a disease of the mushroom crop, are introduced into a production environment where an infection reservoir of a mushroom disease exists, then the new strain(s) of the invention will be relatively more difficult to infect and will provide a tool and an opportunity for a more comprehensive facility hygiene program to eliminate significant reservoirs of disease infection from the facility. The strains of the invention thus enable a method of improving farm hygiene that is not otherwise feasible in today's commercial environment.

More particularly, it is believed that if such strains comprising the invention, for example J10165, combining commercially acceptable traits with the additionally useful trait of incompatibility with strains of the U1 lineage group, are introduced into a production environment where an infection reservoir of a mushroom virus exists within living matter (such as spent compost, mycelial fragments or dust, and spores) of a strain belonging to the U1 lineage group, then the new incompatible strain(s) of the invention will be relatively more difficult to infect and will provide a tool and an opportunity for a more comprehensive facility hygiene program to eliminate significant reservoirs of virus infection from the facility. The strains of the invention thus enable a method of improving farm hygiene that is not otherwise feasible in today's commercial environment.

In order to demonstrate practice of this invention, the following prophetic example sets forth how the invention will enable a method of improving mushroom farm hygiene at facilities where commercially accepted white *Agaricus* strains of a particular shared incompatibility type, for example the U1 lineage group, are routinely grown. Surveillance at production facilities can reveal the presence of a virus infection, for example of the LaFrance Isometric Virus (=LIV), in the living material of such a strain group. Subsequent monitoring activities can indicate whether available facility practices are succeeding at eliminating the reservoir of infectious material. By infection reservoir it is understood that living *Agaricus* spores and culture debris and residues including colonized compost, in which functioning virus particles have become incorporated, is meant. If further control measures are indicated to be necessary, a commercially acceptable novel white hybrid *Agaricus* strain having an incompatibility phenotype antagonistic to the infected strain group, and comprising or descended from J9277, for example the J10165 strain, can be introduced into production in the facility to replace the more susceptible strains ordinarily grown there. In practice, either the facility will inoculate compost and casing materials with purchased spawn and/or inocula of a suitable strain comprising or descended from J9277, or will purchase pre-inoculated materials incorporating such a strain from a supplier. At the farm, the new strain of the invention is expected to exhibit a reduced ability to anastomose successfully with living culture debris and residues comprising the reservoir of infections material at the facility, due to mutual antagonism arising from their incompatibility. Incidence of virus infection will therefore be substantially reduced in crops of the new strain. This practice will be followed at the production facility until the facility has entirely replaced the original strain(s) and replaced it or them with a strain of the invention, and more preferably has produced at least two entire crops of the strain of the invention facility-wide, thus completely displacing materials comprising the virus infection reservoir. At that time, if the infection reservoir has been demonstrably reduced or eliminated, the facility will have the option of returning to production of strains of the original group.

It is to be understood that any variations evident fall within the scope of the claimed invention and thus, the selection of specific hybridization techniques and sources of homokaryons and heterokaryons can be determined without departing from the spirit of the invention herein disclosed and described. Thus, the scope of the invention shall include all modifications and variations that may fall within the scope of the attached claims.

What is claimed is:

1. A method of producing mushroom culture of *Agaricus bisporus* comprising: hybridizing a first strain and a second strain of *Agaricus bisporus*, wherein at least one of said first and second strains of *Agaricus* is selected from the group consisting of a hybrid mushroom culture of *Agaricus bisporus* designated strain J9277, a representative culture of said hybrid strain J9277 having been deposited under ATCC Accession No. PTA-6692.

2. The method according to claim 1, wherein said hybrid mushroom culture exhibits antagonism toward heterokaryon strains in the Horst U1/U3 lineage group.

3. The method according to claim 1, wherein the mushroom culture is provided in mushroom products selected from the group consisting of inoculum, mushroom spawn, casing inoculant, and mushrooms.

4. The method according to claim 1, wherein the mushroom culture is provided in derived cultures selected from the group consisting of homokaryons, heterokaryons, aneuploids, somatic subcultures, tissue explant cultures, protoplasts, live spores, germinating spores, inbred descendants and out crossed descendants, and transgenic lines.

5. The method according to claim 1, further comprising: repeating the hybridization process of claim 1 for up to four generations of crosses.

6. The method according to claim 5, wherein the mushroom culture is provided in mushroom products selected from the group consisting of inoculum, mushroom spawn, casing inoculant, and mushrooms.

7. The method according to claim 5, wherein the mushroom culture is provided in derived cultures selected from the group consisting of homokaryons, heterokaryons, aneuploids, somatic subcultures, tissue explant cultures, protoplasts, live spores, germinating spores, inbred descendants and out crossed descendants, and transgenic lines.

\* \* \* \* \*